United States Patent
Gross

(10) Patent No.: US 8,692,181 B2
(45) Date of Patent: Apr. 8, 2014

(54) MEDICAL IMAGING EQUIPMENT AND A MEASURING METHOD FOR DETECTING THE POSITION OF A CONVEYING DEVICE OF THE MEDICAL IMAGING EQUIPMENT

(75) Inventor: Patrick Gross, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 369 days.

(21) Appl. No.: 12/969,625

(22) Filed: Dec. 16, 2010

(65) Prior Publication Data

US 2011/0147611 A1 Jun. 23, 2011

(30) Foreign Application Priority Data

Dec. 18, 2009 (DE) .......................... 10 2009 054 916
May 19, 2010 (DE) .......................... 10 2010 020 923

(51) Int. Cl.
*G06M 7/00* (2006.01)
*A47B 13/00* (2006.01)

(52) U.S. Cl.
USPC .............................. 250/221; 5/601

(58) Field of Classification Search
USPC ............................... 250/221; 356/4.01; 5/601
See application file for complete search history.

(56) References Cited

U.S. PATENT DOCUMENTS

| | | | |
|---|---|---|---|
| 6,460,206 B1 | 10/2002 | Blasche et al. | |
| 7,375,822 B2 * | 5/2008 | Tsai | 356/498 |
| 8,107,056 B1 * | 1/2012 | Riza | 356/4.05 |
| 2004/0206894 A1 * | 10/2004 | Oka et al. | 250/231.13 |
| 2007/0171428 A1 | 7/2007 | Dunham | |
| 2008/0144000 A1 * | 6/2008 | Thun et al. | 356/5.05 |

FOREIGN PATENT DOCUMENTS

| | | |
|---|---|---|
| DE | 102007005699 A1 | 8/2008 |
| DE | 102008006711 A1 | 8/2009 |
| EP | 0501795 A2 | 9/1992 |

* cited by examiner

*Primary Examiner* — Thanh Luu

(57) ABSTRACT

A medical imaging equipment has a conveying device that can be moved at least partially in at least one direction. A position-detecting device has at least one transmitting element which detects a position of the conveying device and emits position-measuring radiation. The position-detecting device has at least one detector element. The position-detecting device has at least one semi-transparent reflector element.

18 Claims, 4 Drawing Sheets

MEDICAL IMAGING EQUIPMENT AND A MEASURING METHOD FOR DETECTING THE POSITION OF A CONVEYING DEVICE OF THE MEDICAL IMAGING EQUIPMENT

CROSS REFERENCE TO RELATED APPLICATIONS

This application claims priority of German application No. 10 2009 054 916.1 filed Dec. 18, 2009 and German application No. 10 2010 020 923.6 filed May 1, 2010, both of the applications are incorporated by reference herein in their entirety.

FIELD OF THE INVENTION

The present invention relates to medical imaging equipment having a conveying device that can be moved at least partially in at least one direction, and a position-detecting device, comprising at least one transmitting element which for detecting the position of the conveying device emits position-measuring radiation, and at least one detector element.

BACKGROUND OF THE INVENTION

Medical imaging equipment having a conveying device that is movable in at least one direction is already known. The medical imaging equipment, by way of example a magnetic resonance tomography apparatus, a computerized tomography apparatus and/or a PET apparatus, is very accurate and this requires precise determination of a position of the conveying device in order to be able to carry out a treatment and/or an examination. In this connection a patient is moved into a receiving region of medical imaging equipment by means of the conveying device, the conveying device preferably comprising a mobile patient couch which is arranged so as to be movable in at least one direction. The medical imaging equipment comprises a position-detecting device for detecting the position of the movable conveying device.

In a conventional position-detecting device a position of the conveying device is detected by means of an encoder which is arranged in a drive unit of the conveying device and/or is coupled thereto. However, there is a great inaccuracy in the detected position of the conveying device with this method.

A further known position-detecting device comprises thread take-ups which are also moved as the conveying device is moved. This movement of the thread take-ups is detected and the position of the conveying device determined therefrom. However, this method has the drawback that owing to an elasticity and/or a stretching of a material of the thread take-ups the detected position of the conveying device is highly inaccurate.

A position-detecting device comprising optical sensors and/or controllers for determining and/or detecting a movement and/or position of the conveying device is also known. However, this method has the drawback that these sensors and/or controllers are arranged at least partially within the receiving region and are therefore exposed to treatment and/or examination radiation. This can undesirably impair both treatment and position detection.

A further known position-detecting device of medical imaging equipment, moreover, comprises a laser system which includes a laser source for emitting a laser signal and a detector element for receiving the laser signal. The laser signal is beamed directly from the laser source onto the detector element in this case. Conventional measuring methods, such as a time of flight method by way of example, are very imprecise in terms of position detection, however. Furthermore, the laser source and/or the detector element are arranged on the movable conveying device and are therefore exposed to examination radiation.

SUMMARY OF THE INVENTION

The present invention is based in particular on the object of providing medical imaging equipment which allows precise detection of a position of the conveying device. The object is achieved by the features of the independent claims. Advantageous embodiments are described in the dependant claims.

The invention proceeds from medical imaging equipment having a conveying device that can be moved at least partially in at least one direction, and a position-detecting device, comprising at least one transmitting element which for detecting the position of the conveying device emits position-measuring radiation, and at least one detector element.

It is proposed that the position-detecting device comprises at least one semi-transparent reflector element. The medical imaging equipment is formed in particular by a magnetic resonance tomography apparatus, a computerized tomography apparatus and/or a PET apparatus and comprises a receiving region in which an imaging medical examination can take place on an object for examination, in particular on a patient. In this connection a semi-transparent reflector element should in particular be taken to mean an element by means of which a first radiation fraction of incident radiation, in particular the incident position-measuring radiation, may be reflected and a further radiation fraction of the incident radiation may be transmitted by the semi-transparent reflector element. The semi-transparent reflector element can, by way of example, be formed by a semi-transparent mirror and/or in a particularly compact manner by a semi-transparent foil and/or a semi-transparent coating which is applied to a detector surface. The position-detecting device can, moreover, comprise a plurality of detector elements which are particularly advantageously arranged within a detector array. A distance from the transmitting element and/or detector element to the conveying device, in particular a reference point of the conveying device, may advantageously be precisely detected by way of the embodiment according to the invention in that radiation fractions having a different path length between transmitting element and detector element may be detected. Following each impingement of the position-measuring radiation on the semi-transparent reflector element the radiation fraction transmitting the semi-transparent reflector element may be detected and the radiation fraction reflected by the semi-transparent reflector element has to be transmitted again through at least twice the path length between the semi-transparent reflector element and a further reflector element before it strikes the semi-transparent reflector element again.

It is also proposed that the semi-transparent reflector element is arranged upstream of the detector element along a radiation path of the position-measuring radiation. The semi-transparent reflector element is in the process arranged inside the position-detecting device in such a way that a length of the single radiation path from the transmitting element to the semi-transparent reflector element substantially matches a length of the single radiation path from the transmitting element to the detector element. A radiation fraction that penetrates the semi-transparent reflector element can be directly detected by the detector element and, moreover, an advantageous multiplicity of a length of a distance that is to be detected may be achieved, and therewith minimization of an inaccuracy in the distance to be detected.

An advantageous multiplicity of the distance to be detected, in particular a position of a reference point of the conveying device with respect to the transmitting element and/or detector element, may also be achieved if the position-detecting device comprises a further reflector element. In an advantageous development of the invention the further reflector element can be formed by a retroreflector element in which the incident radiation is reflected substantially in a direction back to a radiation source of the incident radiation. An alternative embodiment of the further reflector element is also always possible.

If a beam direction of the position-measuring radiation is oriented substantially orthogonally to a reflective surface of at least one of the reflector elements, a particularly compact construction of the position-detecting device may be achieved for high multiplicity of a path length of the distance. A position-detecting device designed in this way may be used particularly advantageously in the medical imaging equipment formed by a magnetic resonance tomography apparatus as in this case the installation space available for the position-detecting unit is limited. A beam guide of a beam striking the reflector element and a beam guide of a beam of the position-measuring radiation reflected by the reflector element are arranged substantially parallel to each other in this case. Furthermore, the incident beam and the reflected beam of the position-measuring radiation are at least partially overlaid along the radiation path. Radiation fractions in one direction which have covered different path lengths may also be overlaid.

A reflective surface of the semi-transparent reflector element is particularly advantageously oriented substantially parallel to a reflective surface of the at least one further reflector element, so even in the case of multiple reflections between, by way of example, the semi-transparent reflector element and the further reflector element, substantially parallel beam guidance of the reflected beam and of the incident beam may be achieved.

The transmitting element and/or the detector element may be arranged on the movable conveying device to detect the position of the conveying device. However, the further reflector element is particularly advantageously arranged on the movable conveying device. The transmitting element and/or the detector element can consequently be arranged outside of the receiving region of the medical imaging equipment, so only the further reflector element has to satisfy the strict requirements that are necessary for interference-free operation of the medical imaging equipment, such as, by way of example, a magnetic resonance-compatible design of the further reflector element.

In an advantageous development of the invention it is proposed that the medical imaging equipment comprises a receiving region to receive the movable conveying device, with the at least one transmitting element and/or the at least one detector element being stationarily arranged outside of the receiving region. Inexpensive transmitting and/or detector elements in particular may therefore be used which are arranged substantially outside of a region penetrated by an examination area or examination radiation. Furthermore, additional cable, which has to be moved with the conveying device and which would be necessary in the event of an arrangement of the transmitting element and/or detector element on the movable conveying device, may advantageously be omitted. In particular the transmitting element and the detector element are arranged on the housing of the medical imaging equipment on the same opening side of the receiving region and particularly preferably on a common printed circuit board arranged on the housing, so an advantageous time control for position detection between the transmitting element and the detector element may be achieved. The semi-transparent reflector element is particularly advantageously also stationarily arranged outside of a receiving region for receiving the movable conveying device.

The position-detecting device particularly advantageously comprises a further optical element which is arranged along a radiation path from the transmitting element to the detector element upstream of the detector element for focusing the position-measuring radiation onto the detector element. Slight beam deviations may advantageously be compensated so the position-measuring radiation can always be detected by the detector element for a position-detection measurement. The further optical element can, by way of example, be formed by a lens and/or a parabolic minor and/or further optical elements that seem sensible to a person skilled in the art.

It is also proposed that the position-detecting device comprises at least one modulation unit which is provided for modulation of a radiation parameter of the position-measuring radiation. The radiation parameter is formed, by way of example, by a frequency and/or a polarization and/or an amplitude of the position-measuring radiation. The radiation parameter is preferably modulated periodically over a time. A distance can advantageously be measured using a phase shift between a detected radiation parameter and a radiation parameter of the position-measuring radiation emitted at the detection instant.

The invention also proceeds from a measuring method for detecting the position of a conveying device of medical imaging equipment, position-measuring radiation being emitted in an emission step by means of at least one transmitting element of the medical imaging equipment, and in a detection step the position-measuring radiation is detected by means of at least one detection element of the medical imaging equipment.

It is proposed that a first radiation fraction of the position-measuring radiation is transmitted along a radiation path between the emission step and the detection step on at least one semi-transparent reflector element and that a second radiation fraction of the position-measuring radiation is reflected at the semi-transparent reflector element. One radiation fraction can therefore be detected by the detector element and a further radiation fraction can be available to pass through a further reflection path. A distance from the transmitting element and/or the detector element to the conveying device, in particular a reference point of the conveying device, may advantageously be precisely detected hereby in that the distance may be detected with a different level of multiplicity of a path length of the distance, and therefore a method-dependent inaccuracy when determining the distance may be minimized.

It is also proposed that the position-measuring radiation is reflected at least one further reflector element, whereby a high multiplicity of a path length of the distance to be detected and/or a path length covered by the conveying device may be achieved and the accuracy of the position to be detected and/or a distance to be detected may be increased in this way.

It is also proposed that the first radiation fraction of the position-measuring radiation is detected following a transmission. A radiation fraction of the position-measuring radiation may advantageously be detected after each passage through a reflection path of the position-detecting device, so radiation fractions with a different path length between the transmitting element and the detector element may be detected. This may be achieved particularly advantageously if the second radiation fraction of the position-measuring radiation is reflected by the semi-transparent reflector element onto the further reflector element.

The different radiation fractions of the position-measuring radiation are particularly advantageously successively detected following a different number of reflections. A systematic, in particular constant, inaccuracy in a measuring method in relation to determination of a distance and/or a position may be minimized in that a path length of a distance may be detected several times with a multiplicity of the path length at different levels. A movement and/or a position of the conveying device with respect to a housing of the magnetic resonance apparatus can be determined particularly precisely in this way.

It is also proposed that at least one time signal is detected in the detection step, whereby a position of the conveying device may advantageously be detected using a running time. The running time may be formed by a running time between an emission time and the detection time of the position-measuring radiation or by a running time between two radiation fractions successively striking the detector element with a different number of reflections respectively.

If a signal characteristic of the position-measuring radiation is at least partially detected to control triggering, a trigger threshold for activating a detection process may advantageously be adjusted at, by way of example, a reducing signal strength. Signal components with a high number of reflections, and therefore a particularly low signal strength, may in particular be advantageously detected in this way.

It is also proposed that a radiation parameter of the position-measuring radiation is modulated before the emission step, whereby a distance can advantageously be measured using a phase shift between a detected radiation parameter and a radiation parameter of the position-measuring radiation emitted at the detection instant.

In an advantageous development of the invention it is proposed that the radiation parameter is modulated at a modulation frequency. The modulation frequency is preferably formed by an angle frequency. A maximum receiving signal can be detected in the detector element and/or en electronic evaluation device if the modulation frequency is an integral multiple of pi $\pi$, so all signal components striking the detector element at one time oscillate in phase.

The position-measuring radiation is particularly advantageously emitted in the emission step with a beam direction which is substantially orthogonal to a reflective surface of a reflector element, whereby a particularly compact construction of the position-detecting device may be achieved for a high multiplicity of a path length of a distance to be detected. Furthermore, a beam striking the reflective surface and a beam of the position-measuring radiation reflected by the reflective surface are at least partially mutually overlaid along the radiation path.

It is also proposed that the position-measuring radiation is emitted with a beam direction which encloses an angle of greater than 0° to a surface normal of a reflective surface of a reflector element. The angle is preferably dependent on a maximum number of reflections of the position-measuring radiation along a radiation path from the transmitting element to the detector element. Furthermore, the angle can be dependent on a width of the reflective surface and/or a width of the detection area, so the reflective surface and/or the detection area may be effectively used. Inaccuracies in a measuring method may therefore be detected particularly exactly and a distance precisely determined therefore.

BRIEF DESCRIPTION OF THE DRAWINGS

Further advantages emerge from the following description of the drawings. Exemplary embodiments of the invention are shown in the drawings. The drawings, description and claims contain numerous features in combination. A person skilled in the art will expediently also consider the features individually and combine them into sensible further combinations.

In the drawings.

DETAILED DESCRIPTION OF THE INVENTION

Figure 1:
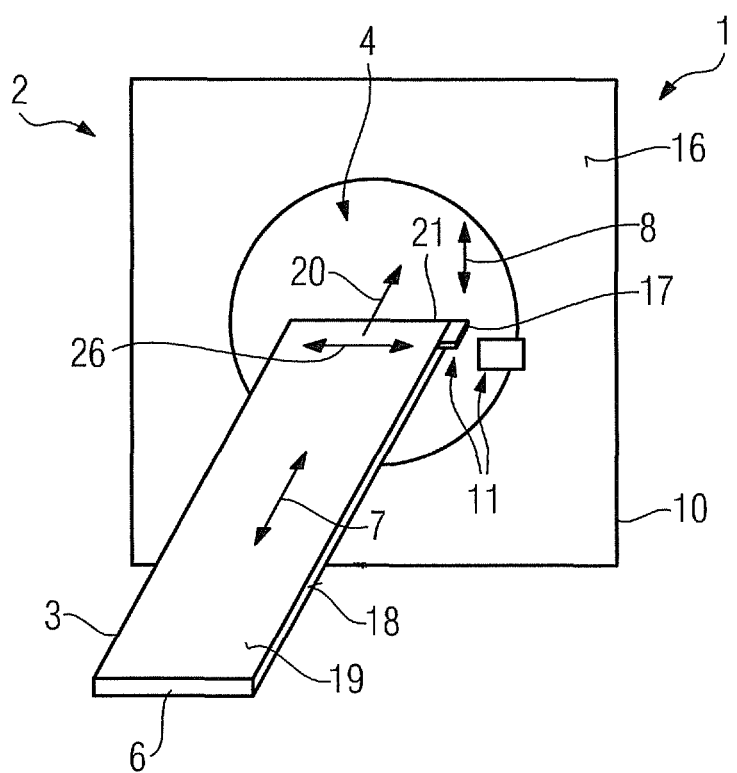
FIG. 1 shows inventive medical imaging equipment in a schematic view.

FIG. 1 shows inventive medical imaging equipment 1 which is formed by a magnetic resonance tomography apparatus 2. The magnetic resonance tomography apparatus 2 comprises a main magnet (not shown in detail) for producing a strong and constant magnetic field. The magnetic resonance tomography apparatus 2 also comprises gradient coils (not shown in detail), which are provided to produce a linear gradient field, and high frequency coils (not shown in detail). The magnetic resonance tomography apparatus 2 also comprises a receiving region 4 for receiving an object for examination and/or a patient for an imaging examination. In an alternative embodiment the medical imaging equipment 1 can also be formed by a computerized tomography apparatus and/or a PET apparatus.

The medical imaging equipment 1 also comprises a conveying device 3, which includes a patient couch 6 and is movably arranged in a z-direction 7. The z-direction 7 runs parallel to a surface normal of a receiving opening of the cylindrical receiving region 4. In a further embodiment of the invention it is, moreover, always conceivable for the conveying device 3 to be movably arranged in further directions, such as, by way of example, in a y-direction 8 and/or an x-direction 26. Together the x-direction 26, the y-direction 8 and the z-direction 7 form an orthogonal system. The object for examination and/or the patient is moved in or out of the receiving region 4 in the z-direction 7 by means of the conveying device 3, on which the object for examination and/or patient may be positioned so as to be reclined.

During operation of the medical imaging equipment 1 a region is selected for examination. The region for examination includes a selective layer or a plurality of selective layers which may be chosen by a person carrying out the treatment using the medical imaging equipment 1. During operation of the medical imaging equipment 1 a volume for examination of the patient is to be imaged using these selective layers. Information about an exact position of the volume for examination and/or of the patient is required for this purpose. For this reason the medical imaging equipment 1 comprises a position-detecting device 11 which is designed to detect the position of the conveying device 3.

Figure 2:
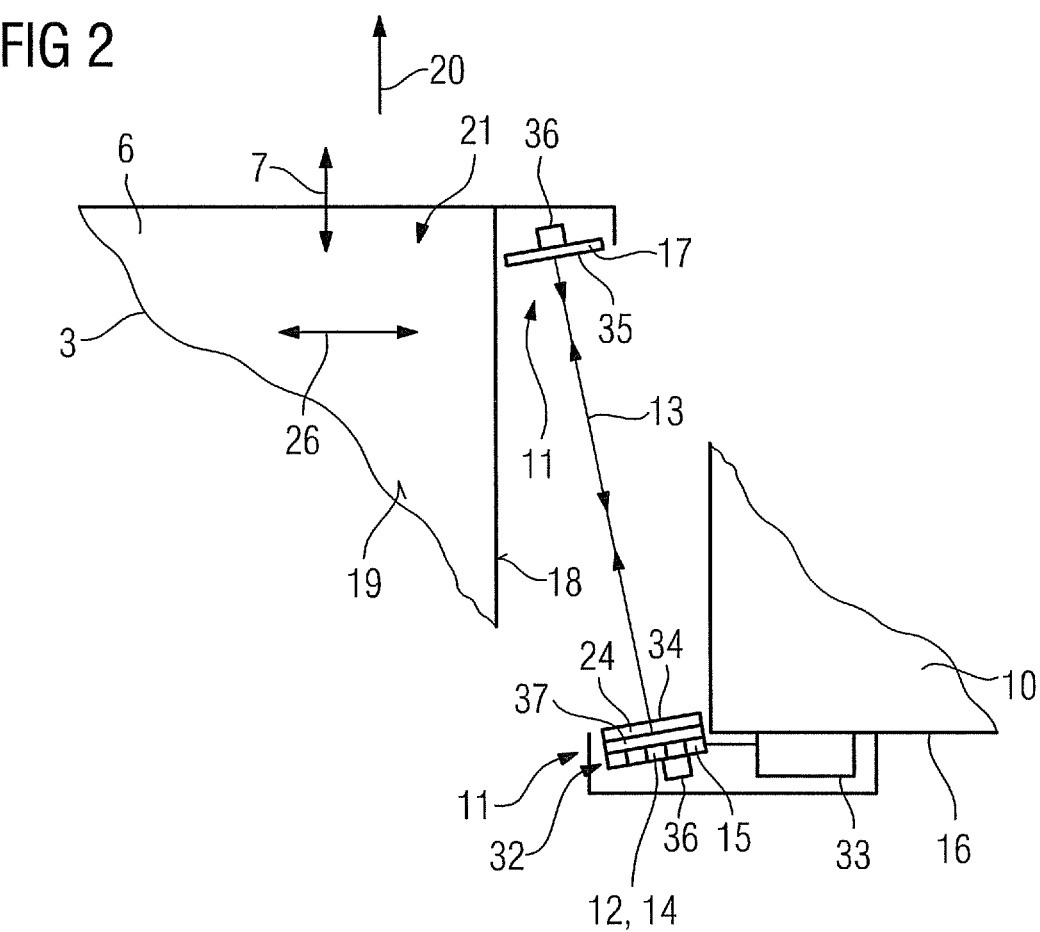
FIG. 2 shows a schematic detailed view of a position-detecting device and a conveying device of the medical imaging equipment.

The position-detecting device 11 is shown in FIG. 2 in more detail and comprises a transmitting element 12 for emitting position-measuring radiation 13. The transmitting element 12 comprises a laser source 14, so the position-measuring radiation 13 formed by laser radiation is emitted during operation of the position-detecting device 11. The laser source 14 provides universally employable position-measuring radiation 13 which in this case can incorporate all types of laser radiation known to a person skilled in the art, such as, by way of example, infrared laser radiation, microwave laser radiation, etc. The position-detecting device 11 also comprises a detector array 32 having a plurality of detector elements 15 for detecting the position-measuring radiation 13 emitted by the transmitting element 12. The transmitting element 12 is arranged in a plane with the individual detector elements 15 of the detector array 32, the transmitting element 12 being surrounded by the individual detector elements 15 and therefore constituting a central element with respect to the detector elements 15. Both the transmitting element 12 and the detector array 32 are stationarily arranged on a housing 10 of the medical imaging equipment 1 outside of the receiving region 4. The transmitting element 12 and the detector array 32 are arranged on the same side of the housing 16 of the medical imaging equipment 1 and are integrated on a common printed circuit board. In an alternative embodiment the transmitting element 12 and the detector array 32 may also be arranged side by side. Furthermore, the transmitting element 12 and the detector array 32 are arranged at a level of the conveying device 3, in particular the patient couch 6 of the conveying device 3, in the y-direction 8 of the medical imaging equipment 1. The position-detecting device 11 also comprises an electronic evaluation device 33 with a computer unit which is provided for evaluating the data detected by the detector array 32.

The position-detecting device 11 also comprises a semi-transparent reflector element 24 which, together with the transmitting element 12 and the detector array 32, is stationarily arranged outside of the receiving region 4. The semi-transparent reflector element 24 is arranged along a radiation path of the position-measuring radiation 13 from the transmitting element 12 to the detector array 32 upstream of the detector array 32. The semi-transparent reflector element 24 is in the process arranged upstream of the detector array 32 in such a way that the position-measuring radiation 13 can radiate from the semi-transparent reflector element 24 directly onto the detector array 32 without being deflected again.

For focusing the position-measuring radiation 13 onto the detector array 32 the position-detecting device 11 comprises a further optical element 37 which is arranged along the radiation path from the transmitting element 12 to the detector array 32 between the semi-transparent reflector element 24 and the detector array 32. The further optical element 37 is formed, by way of example, by an optical lens and/or a parabolic mirror. The semi-transparent reflector element 24 can be formed, by way of example, by a semi-transparent mirror and/or a semi-transparent coating which is applied to the further optical element 37. The further optical element 37 is permeable to radiation in the direction from the transmitting element 12 to the semi-transparent reflector element 24.

The position-detecting device 11 comprises a further reflector element 17 which is arranged on the conveying device 3 that is movable in the z-direction 7, and in particular on the patient couch 6. The further reflector element 17 is arranged on a side face 18 of the patient couch 6 which is oriented substantially perpendicularly to a lying surface 19 of the patient couch 6, so the reclining comfort of the patient is unaffected during treatment and/or examination. The further reflector element 17 is, moreover, arranged on the conveying device 3 along a longitudinal extension of the conveying device 3 substantially at a leading end region 21 in an introductory movement direction 20. The longitudinal extension of the conveying device 3 is oriented parallel to the z-direction 7. The introductory movement direction 20 represents a direction of movement of the conveying device 3 as it is introduced into the receiving region 4. Basically an arrangement of the reflector element 17 on a trailing end region and/or on further regions of the conveying device 3 that seem sensible to a person skilled in the art is always conceivable.

The further reflector element 17 is formed, by way of example, by a retroreflector element in which incident radiation is substantially reflected in a direction back to a radiation source of the incident radiation. The two reflector elements 17, 24 are arranged in relation to each other in such a way that a reflective surface 34, 35 of the respective reflector element 17, 24 is arranged at a side of the reflector element 17, 24 that faces the respective other reflector element 17, 24. The two reflective surfaces 34, 35 of the two reflector elements 17, 24 are, moreover, arranged substantially parallel to each other. For this purpose the two reflector elements 17, 24 each comprise an adjusting means 36, which, by way of example, is formed by an acceleration sensor and automatically adjusts an orientation of the reflective surface 34, 36 in relation to gravity. The reflector elements 17, 24 can comprise further adjusting means 36, moreover, which are provided for, in particular, automatic orientation of the respective reflector element 17, 24 in relation to a further direction preferably oriented perpendicularly to gravity.

Figure 3:
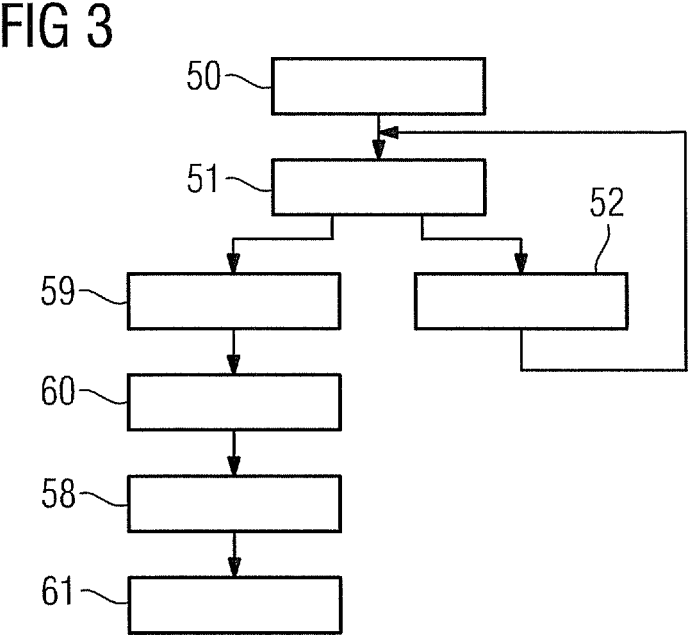
FIG. 3 shows a flow chart of a first inventive method, FIG. 4 schematically shows a detailed view as an alternative to FIG. 2 of the position-detecting device and the conveying device.

During operation of the position-detecting device 11 together with the medical imaging equipment 1 the position-measuring radiation 13 is firstly emitted by the transmitting element 12 in an emission step 50 to detect the position of the conveying device 3 (FIG. 3). A beam direction of the position-measuring radiation 13 runs substantially orthogonally to the reflective surface 35 of the further reflector element 17 in the direction of the further reflector element 17. The position-measuring radiation undergoes a first reflection 51 at the further reflector element 17, the position-measuring radiation 13 being reflected back substantially in a direction of the transmitting element 12 or of the semi-transparent reflector element 24. The radiation path of the position-measuring radiation 13 from the transmitting element 12 to the further reflector element 17 is substantially parallel to the radiation path of the position-measuring radiation 13 from the further reflector element 17 to the semi-transparent reflector element 24. A first radiation fraction of the position-measuring radiation 13 undergoes a transmission 59 at the semi-transparent reflector element 24 and firstly strikes the further optical element 37. At this location the first radiation fraction is focused 60 onto the detector array 32 and is detected on it in a subsequent detection step 58.

A second radiation fraction of the position-measuring radiation 13 undergoes a reflection 52 at the semi-transparent reflector element 24 and is reflected back in the direction of the further reflector element 17, the radiation path of the second radiation fraction also being oriented substantially orthogonally to the reflective surface 35 of the further reflector element 17. At the further reflector element 17 the reflection 51 of the position-measuring radiation 13 again occurs in the direction of the semi-transparent reflector element 24. At the semi-transparent reflector element 24 transmission 59 of a radiation fraction of the position-measuring radiation 13 again takes place in the direction of the detector array 32 and a reflection 54 of a further radiation fraction of the position-measuring radiation 13 back to the further reflector element 17. Following the transmission 59, a focusing 60 and a detection step 58 of the position-measuring radiation 13 again take place. A transmission coefficient for the transmission 59 at the semi-transparent reflector element 24 can, by way of example, be 0.1, so 10% respectively of the radiation striking the semi-transparent reflector element 24 is transmitted and 90% of the radiation striking the semi-transparent reflector element 24 is reflected. A signal amplitude of the detected signal components becomes smaller as the number of reflections 51, 52 increases.

In the emission step 50 the position-measuring radiation 13 is emitted in the form of a pulse signal. This pulse signal or signal components of the pulse signal is/are detected in detection step 58 at a sampling rate f. The sampling rate f is determined by the following calculation:

$$f > 2/2 \cdot dx/c.$$

C is the speed of light, $(2 \cdot dx/c)$ indicates the additional running time of the pulse signal in the event of a change dx in the path length. The factor 2 results for a complete image formation of a signal at a sampling rate that is constant over time, with a sampling rate that is more than twice as great as a signal frequency being required here. The sampling rate f must therefore be about 600 GHz in the case of a desired spatial resolution dx of about 0.5 mm.

The different radiation fractions of the position-measuring radiation 13 are each successively detected in a plurality of detection steps 58 following a different number of reflections 51, 52. The computer unit includes a trigger unit which generates a time signal using a difference in time between two successively detected signals at the detector array 32 and/or using a time signal for emitting the position-measuring radiation 13 and a subsequent detected signal at the detector array. Using the time signal a distance and/or a position of the conveying device 3 is then determined in an evaluation step 61 which follows the detection step 58. An emission time for emission of the position-measuring signal 13 by the emission element 12 and a detection time for detection of a signal component by the detector array 32 are detected for this purpose by the trigger unit and/or the electronic evaluation device. Optimally exact knowledge of the signal to be detected is necessary for correct resolution of a trigger signal of the trigger unit, such as, by way of example a signal characteristic of the radiation fraction striking the detector array 32. A start edge and/or an end edge of the signal characteristic is/are preferably detected here. A trigger threshold for detecting the detected signal component at a reducing signal amplitude may also be adapted by the trigger unit by means of the detected signal characteristic in evaluation step 61.

It is also conceivable that, owing to the short distances between the individual signal pulses which strike the detector array 32, only every second signal pulse striking the detector array 32 is detected and a number of reflections or a path length covered between the transmitting element and the detector array 32 also enter into the calculation of the position of the conveying device 3. By way of example, the trigger unit can only be available again for further data recording following 1.5 times the signal propagation time of the first signal component from transmitting element 12 to detector array 32, so the next signal component detected by the electronic evaluation device has passed through the reflective section of the first signal component three times. A time between two signal components detected by the electronic evaluation device 33 can also be induced by two different and successively emitted pulse signals. The position of the conveying device 3 can also be detected several times using a plurality of time signals in evaluation step 33 and an inaccuracy in the position-measuring device 11 that enters the determination of the position of the conveying device 3 can be minimized.

The volume to be examined can therefore be brought at least partially into spatial congruity with the examination area as exactly as possible in that an exact change in the position of the conveying device 3 is possible owing to precise position detection. A precise position of the conveying device 3 and therewith of the patient can therefore be detected for a positioning, in particular when imaging larger areas and/or organs by means of the medical imaging equipment 1, in which a movement of the patient is required for complete imaging. The precision of the position detection of the conveying device 3 is determined by a number of reflections 51, 52 of the position-measuring radiation 13, accuracy of position detection increasing with the number of reflections 51, 52 of the position-measuring radiation 13. The position of the patient couch 6 is absolutely determined by the computer unit in this case so that additional reference measurements may be avoided for a relative position determination of the patient couch 6.

FIGS. 4 to 7 show alternative exemplary embodiments of the invention. Components, features and functions that are substantially the same are basically denoted by the same reference characters. The following description is substantially limited to the differences from the exemplary embodiment in FIGS. 2 and 3, reference being made to the description of the exemplary embodiment in FIGS. 2 to 3 in relation to components, features and functions that are substantially the same.

Figure 4:
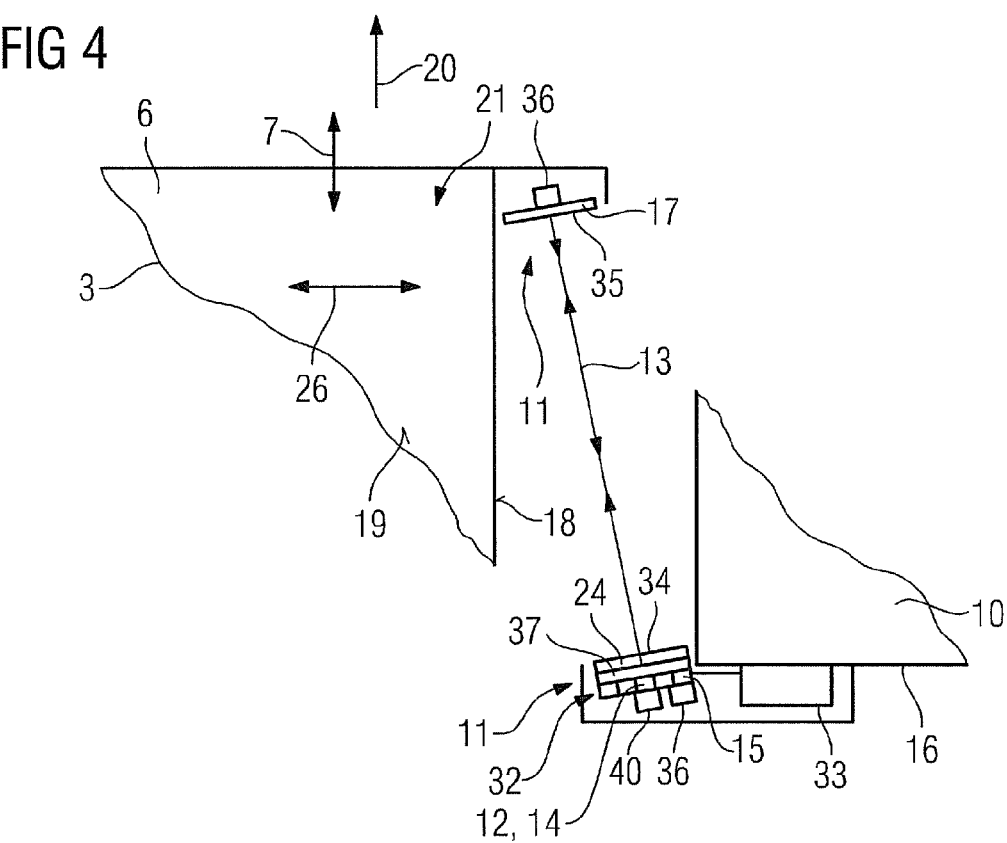
Figure 5:
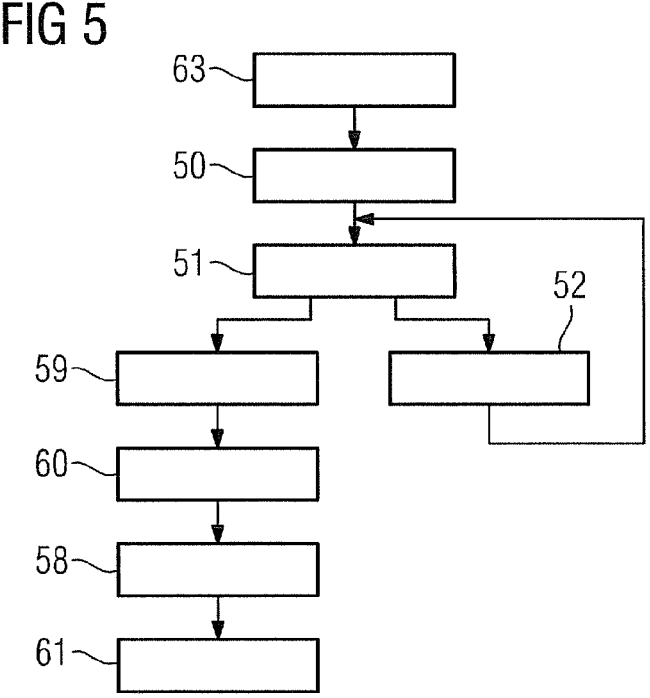
FIG. 5 shows a flow chart of a second inventive method.

FIGS. 4 and 5 show a position-detecting device 11 and method for determining a position of a conveying device 3 alternative to those in FIGS. 2 and 3. The position-detecting device 11 in FIG. 4 comprises all components and units of the position-detecting device in FIG. 2 and additionally a modulation unit 40, by means of which a radiation parameter of the position-measuring radiation 13 may be modulated. The radiation parameter can, by way of example, be formed by a frequency and/or of polarity and/or an amplitude, etc.

The method according to FIG. 5 will be described hereinafter with reference to a frequency modulation. The same applies, however, to an amplitude modulation and/or a polarization modulation. The frequency of the position-measuring radiation 13 is continuously modulated within a frequency range in a modulation step 63. This modulation of the frequency takes place periodically at a modulation frequency $f_m$. In the emission step the position-measuring radiation 13 is then emitted by the transmitting element 12. A detection step 58, reflections 51, 52 and transmissions 59 with subsequent focusing 60 take place analogously to the method in FIG. 3.

The position-measuring radiation 13 passes through a radiation path with a reflection 51 or plurality of reflections 51 at a further reflector element 17 and at least one or more reflection(s) 52 and transmission(s) 59 at the semi-transparent reflector element 24 according to the embodiments in FIG. 3. Signal components of the position-measuring radiation 11 are then detected at the detector array 32 at a detection instant in detection step 58, the signal components having a frequency which is different to a further frequency of the position-measuring radiation 13 simultaneously emitted by the transmitting element 12 at the detection instant. A phase shift q between the detected frequency and the simultaneously emitted frequency is determined in the computer unit as follows by means of the modulation frequency $f_m$:

$$q = (2x/c)(2\pi \cdot f_m).$$

Here the factor $(2x/c)$ corresponds to a time which the position-measuring radiation 13 requires for covering a distance x from the transmitting element 12 across the further reflector element 17 to the detector array 32. The factor ($2\pi \cdot f_m$) corresponds to an angle frequency of the modulation. The position of the conveying device 3 is determined using the phase difference.

In the case of multiple reflections the detector array 32 detects a total number of signals $S_{total}$.

$$S_{total} = \Sigma(k_r exp(r \cdot q))$$

Here r is a number of reflections and $k_r$ an amplitude scaled for the respective reflection 51, 52. If the modulation frequency $f_m$ is an integral multiple of pi $\pi$, all signals at the detector array 32 are in phase and add up to a maximum signal. If, on the other hand, the modulation frequency $f_m$ is a half-integral multiple of pi $\pi$, all signals at the detector array 32 are oriented in antiphase and add up to a minimum signal. To determine the distance the modulation frequency $f_m$ is varied until the above condition is fulfilled and the position of the conveying device 3 is therefore detected.

Figure 6:
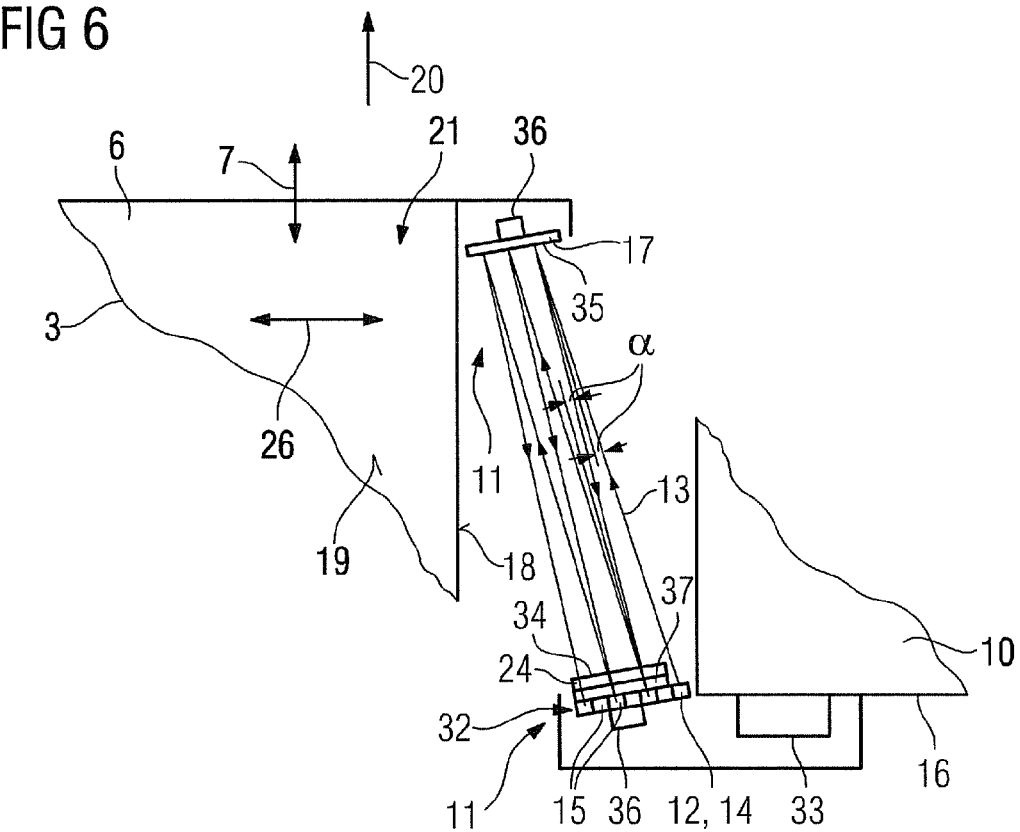
FIG. 6 shows a further, schematic detailed view as an alternative to FIG. 2 of a position-detecting device and a conveying device
Figure 7:
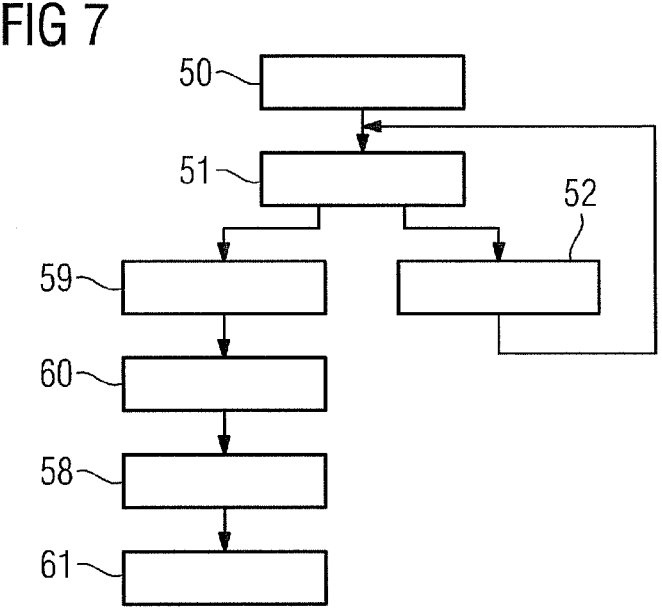
FIG. 7 shows a flow chart of a third inventive method.

FIGS. 6 and 7 show a position-detecting device 11 and a method for determining a position of a conveying device 3 alternative to those in FIGS. 2 and 5. The position-detecting device 11 in FIG. 6 comprises all components and units from FIG. 2, one transmitting element 12 being arranged next to a detector array 32 (FIG. 6). A position of the conveying device 3 is determined by means of a triangulation method according to FIG. 7. Analogously to the description in FIG. 3 the position-measuring radiation 13 is emitted in an emission step 50 and reflected at the further reflector element 17. A detection step 58, reflections 51, 52 and transmissions 59 with subsequent focusing 60 take place analogously to the method in FIG. 3. Relative to a surface normal to the reflective surface 35 of the further reflector element 17 the radiation striking the further reflector element 17 has an angle $\alpha$ which is greater than 0° and continues in the case of the further reflections 51, 52 at the semi-transparent and/or the further reflector element 17, 24. A distance y between an emission location and a detection location of the position-measuring radiation 13 following a reflection 51 at the further reflector element 17 is determined as follows:

$$y = 2x \tan(\alpha)$$

The distance y is therefore dependent on a distance of a reference point of the conveying device 3 from the transmitting element 12 and/or the detector array 32.

In the case of measurements with multiple reflections the individual radiation fractions successively strike the detector array 32, the individual strike sites being arranged side by side on the detector array 32, so a distance $y_r$ after the $r^{th}$ reflection 51, 52 with respect to the emission location is determined according to $$y_r = 2r \cdot x \tan(\alpha)$$

A maximum number of reflections 51, 52 with the reflection angle $\alpha$ is determined by a width of a reflective surface 34, 35 of one of the reflector elements 17, 24 and/or a width of a detector area of the detector array 32. The reflection angle $\alpha$ can, moreover, be selected in such a way that a total width of a reflective surface 34, 35 of one of the reflector elements 17, 24 and/or a total width of a detector area of the detector array 32 is always used for a distance measurement.

The position of the conveying device 3 can in particular be detected especially accurately by means of this method as even very small inaccuracies $d\alpha$ in the angle $\alpha$ between an incident beam and the surface normal of the reflective surface 34, 35 and/or of an orientation of the two reflective surfaces 34, 35 to each other enter the calculation and in this way the errors can be detected and can subsequently be eliminated.

In this regard the distance y is determined according to $$y = x(\tan(\alpha) + \tan(\alpha + d\alpha))$$

and the distance $y_r$ after the $r^{th}$ reflection 51, 52, 53 according to $$y_r = x \left( \tan(\alpha) - \tan(\alpha + rd\alpha) + \sum_{t}^{r} 2\tan(\alpha + td\alpha) \right)$$

However, it is necessary for different radiation fractions of the position-measuring radiation 13 to successively strike the detector element 32 following a different number of reflections 51, 52, 53 and to be detected by the electronic evaluation device 33 in an evaluation step 61.

In a further embodiment of the position-detecting device 11 this may, moreover, comprise a second transmitting element which is arranged at a side of the detector array 32 opposite the first transmitting element 12 and next to the detector array. Position-measuring radiation 13 is emitted by means of the second transmitting element in a direction of the further reflector element which encloses an angle $-\alpha$ between the incident position-measuring radiation of the surface normal of the reflective surface 35. If, in addition, position-measuring radiation is emitted by the second transmitting element the signals striking the detector array 32 can be detected by means of a multiplexer of the electronic evaluation device 33 and be associated with the individual position-measuring radiations of the individual transmitting elements 12.

A combination of the position-detection methods of the exemplary embodiment in FIGS. 6 and 7 with one of the exemplary embodiments in FIGS. 2 to 5 is also conceivable at any time.

In addition to the stationary arrangement of the semi-transparent reflector element 24 on the housing 10 of the medical imaging equipment 1 in FIGS. 1, 2, 4 and 6 an arrangement of the semi-transparent retroreflector element 24 on the movable conveying device 3 together with the detector array 32 is also always conceivable. Furthermore, a reflective surface 34, 35 of at least one of the two reflector elements 17, 24 can have a concave design in order to prevent undesirable beam divergence and/or beam deflection during a measuring operation of the position-detecting device 11.

The invention claimed is:

1. A medical imaging equipment, comprising:
   a conveying device that can be moved at least partially in at least one direction; and
   a position-detecting device comprising:
      a transmitting element that emits a position-measuring radiation,
      a detector array comprising a plurality of detector elements that detects the position-measuring radiation for detecting a position of the conveying device,
      a semi-transparent reflector element that reflects the position-measuring radiation,
   wherein the transmitting element is arranged in a plane with the detector array and is surrounded by the plurality of detector elements,
   wherein the semi-transparent reflector element is arranged stationary outside a receiving region for receiving the movable conveying device.

2. The medical imaging equipment as claimed in claim 1, wherein the semi-transparent reflector element is arranged along a radiation path of the position-measuring radiation upstream of the detector element.

3. The medical imaging equipment as claimed in claim 1, wherein the position-detecting device comprises a further reflector element.

4. The medical imaging equipment as claimed in claim 3, wherein the further reflector element is arranged on the conveying device.

5. The medical imaging equipment as claimed in claim 3, wherein a beam direction of the position-measuring radiation is oriented substantially orthogonally to a reflective surface of the semi-transparent reflector element or a reflective surface of the further reflector element.

6. The medical imaging equipment as claimed in claim 3, wherein a reflective surface of the semi-transparent reflector element is oriented substantially parallel to a reflective surface of the further reflector element.

7. The medical imaging equipment as claimed in claim 1, wherein the transmitting element and/or the detector element is arranged stationary outside a receiving region for receiving the conveying device.

8. The medical imaging equipment as claimed in claim 1, wherein the position-detecting device comprises an optical element that is arranged along a radiation path from the transmitting element to the detector element and is upstream of the detector element for focusing the position-measuring radiation onto the detector element.

9. The medical imaging equipment as claimed in claim 1, wherein the position-detecting device comprises a modulation unit for modulating a radiation parameter of the position-measuring radiation.

10. A measuring method for detecting a position of a conveying device of a medical imaging equipment, comprising:
    emitting a position-measuring radiation by a transmitting element;
    transmitting the position-measuring radiation along a radiation path to a semi-transparent reflector element;
    reflecting the position-measuring radiation by the semi-transparent reflector element;
    detecting the position-measuring radiation by a detection element;
    emitting the position-measuring radiation to a further reflector element,
    reflecting the position-measuring radiation by the further reflector element to the semi-transparent reflector element,
    detecting the position-measuring radiation at the semi-transparent reflector element, and
    reflecting the position-measuring radiation by the semi-transparent reflector element to the further reflector element.

11. The measuring method as claimed in claim 10, wherein the position-measuring radiation is detected at the semi-transparent reflector element after a transmission at the semi-transparent reflector element.

12. The measuring method as claimed in claim 10, wherein a time signal is detected.

13. The measuring method as claimed in claim 10, wherein a signal characteristic of the position-measuring radiation is at least partially detected to control a triggering of the detection.

14. The measuring method as claimed in claim 10, wherein a radiation parameter of the position-measuring radiation is modulated before the emission.

15. The measuring method as claimed in claim 14, wherein the radiation parameter is modulated at a modulation frequency.

16. The measuring method as claimed in claim 10, further comprising:
    successively reflecting the position-measuring radiation by the further reflector element to the semi-transparent reflector element,
    successively detecting the position-measuring radiation at the semi-transparent reflector element, and
    successively reflecting the position-measuring radiation by the semi-transparent reflector element to the further reflector element.

17. The measuring method as claimed in claim 10, wherein the position-measuring radiation is emitted with a beam direction that is substantially orthogonal to a reflective surface of the semi-transparent reflector element or a reflective surface of the further reflector element.

18. The measuring method as claimed in claim 10, wherein the position-measuring radiation is emitted with a beam direction that has an angle between 0° to a surface normal of a reflective surface of the semi-transparent reflector element or a reflective surface of the further reflector element.

* * * * *